United States Patent
Cooke et al.

(10) Patent No.: US 10,272,211 B1
(45) Date of Patent: Apr. 30, 2019

(54) DISPOSABLE TOURNIQUET/SLEEVE WARMER

(71) Applicants: Diane Rubin Cooke, Franklin, TN (US); Cathleen Rearick, Metairie, LA (US)

(72) Inventors: Diane Rubin Cooke, Franklin, TN (US); Cathleen Rearick, Metairie, LA (US)

(*) Notice: Subject to any disclaimer, the term of this patent is extended or adjusted under 35 U.S.C. 154(b) by 413 days.

(21) Appl. No.: 14/153,845

(22) Filed: Jan. 13, 2014

Related U.S. Application Data

(60) Provisional application No. 61/890,531, filed on Oct. 14, 2013, provisional application No. 61/811,003, filed on Apr. 11, 2013.

(51) Int. Cl.
*A61F 7/00* (2006.01)
*A61M 5/42* (2006.01)

(52) U.S. Cl.
CPC ............ *A61M 5/425* (2013.01); *A61M 5/422* (2013.01); *A61M 2205/02* (2013.01); *A61M 2210/005* (2013.01)

(58) Field of Classification Search
CPC ...... A61M 5/425; A61M 5/422; A61M 5/427; A61M 5/44; A61F 2007/0029; A61F 2007/023; A61F 7/08; A61F 2007/0034; A41D 13/0058; A61B 17/1322
See application file for complete search history.

(56) References Cited

U.S. PATENT DOCUMENTS

| | | | |
|---|---|---|---|
| 4,013,070 A * | 3/1977 | Harroff | A61F 5/0109 602/21 |
| 4,229,833 A | 10/1980 | Cox et al. | |
| 4,736,088 A | 4/1988 | Bart | |
| 4,747,409 A * | 5/1988 | Silen | A61F 7/02 607/108 |
| 4,834,802 A * | 5/1989 | Prier | A61B 17/1322 604/113 |
| 5,143,048 A | 9/1992 | Cheney, III | |
| 5,184,613 A | 2/1993 | Mintz | |
| 5,342,412 A | 8/1994 | Ueki | |
| 5,909,801 A | 6/1999 | Coffman | |
| 6,052,824 A | 4/2000 | May | |
| 6,155,263 A | 12/2000 | Weaver | |
| 6,723,115 B1 | 4/2004 | Daly | |
| 7,785,359 B2 * | 8/2010 | Latham | A61F 7/10 607/109 |
| 7,883,487 B2 * | 2/2011 | Shantha | A61K 9/703 604/112 |
| D674,106 S | 1/2013 | Hadash | |

(Continued)

OTHER PUBLICATIONS

"Tourniquet" [Def. 1]. Dictionary.com. Retrieved Mar. 4, 2017, from http://www.dictionary.com/browse/tourniquet.*

*Primary Examiner* — Laura A Bouchelle

(57) ABSTRACT

The present invention relates generally to a warming apparatus such as but not limited to a sleeve with an attached tourniquet that allows for a method of warming human body parts and a method to induce vasodilation to produce the ease of venipuncture. The invention preferably induces vasodilation by applying heat to an area and then further where venipuncture or intravenous catheter insertion is desired, preferably constricting and compressing the veins by bringing them to the surface with the tourniquet.

24 Claims, 8 Drawing Sheets

(56) References Cited

U.S. PATENT DOCUMENTS

| | | |
|---|---|---|
| 2007/0068932 A1* | 3/2007 | Hewes .................... A61F 7/007 219/552 |
| 2008/0045906 A1* | 2/2008 | Grissom ............... A61M 25/02 604/179 |
| 2008/0147152 A1 | 6/2008 | Quincy et al. |
| 2009/0299442 A1 | 12/2009 | Vergona et al. |
| 2011/0314581 A1 | 12/2011 | Gaters |
| 2012/0078223 A1* | 3/2012 | Spiegel ................... A61F 7/034 604/506 |
| 2012/0240918 A1 | 9/2012 | Kirsch et al. |
| 2012/0266351 A1 | 10/2012 | Kim |

* cited by examiner

DISPOSABLE TOURNIQUET/SLEEVE WARMER

CROSS-REFERENCE TO RELATED APPLICATIONS

Priority of U.S. Provisional Patent Application Ser. No. 61/811,003, filed Apr. 11, 2013, and U.S. Provisional Patent Application Ser. No. 61/890,531, filed Oct. 14, 2013, incorporated herein by reference, is hereby claimed.

STATEMENT REGARDING FEDERALLY SPONSORED RESEARCH OR DEVELOPMENT

Not applicable

REFERENCE TO A "MICROFICHE APPENDIX"

Not applicable

BACKGROUND OF THE INVENTION

1. Field of Invention

The present application relates generally to a disposable self-warming apparatus with attached tourniquet that preferably allows for a method of warming human body parts to induce vasodilation resulting in vessel engorgement and increased local blood pressure to foremost produce the ease of venipuncture. More specifically, the invention relates to a disposable apparatus that preferably fastens to a distal extremity such as the hand and forearm for first warming the back of the skin, including veins, arteries, and capillaries; and then, using the tourniquet to slow venous blood flow from the intended site to preferably cause vessel engorgement, raise the local blood volume and pressure of the distal extremity, wherein a clinician could preferably identify an injection or insertion site.

Because of the treatment and procedures performed on distal extremities that share the requirement for vasodilation and reduction of venous blood flow the device design, material and function could be utilized to facilitate limb perfusion for localized intensive treatment, or to increase local blood pressure to promote blood flow path emboli/thrombi of distal extremities.

2. General Background

Achieving vasodilation in preparation for venipuncture can often be difficult for medical practitioners specifically in compromised patients. Causes for difficulty range from cold body temperature, obesity, pre-existing medical conditions, shock, patient's fear of pain, age, etc.

Venipuncture is a common medical procedure that is practiced in Patient Care Facilities where medical practitioners draw blood, insert intravenous catheters, and even provide intravenous feeding or medications. The procedure is typically performed by securing a loose tourniquet around the patient's limb, to constrict the blood flow through the veins, and causing the dilation of the veins, known as vasodilation. Once vasodilation is achieved, the vein is located and punctured with a needle or catheter, a process known as venipuncture.

Therapists and Technicians at Hospitals, Blood Clinics, Surgical Centers, Urgent Care Centers, Laboratories, Doctor's Offices, and all Phlebotomists perform numerous blood tests on people of all ages, gender, race, size, and other factors for many reasons. It is a known fact that in an effort to keep bacteria and viruses down in these settings, the temperature is kept low, typically below 66 degrees Fahrenheit. Chilling patients is the unfortunate outcome. With cold temperatures, there are many patients in which the nurse or Phlebotomist drawing blood will have difficulty finding or getting the needle into the vein, causing multiple blood draw attempts, trauma to the skin and veins, not to mention the patient's emotional state. Cold body temperature causes vasoconstriction decreasing the diameter for the vessel and thus the ability to successfully enter the lumen of the vein. Some people have veins that are quite small and difficult to access, naturally, without the aid of temperature.

Some veins are scarred from repeated punctures to the vein or occluded (blocked). People undergoing chemotherapy, for example, and those being monitored for side effects while taking warfarin (blood thinners), may have more difficulty during a blood draw because their veins have been punctured so often. Obese patients often have difficulty when medical practitioners are beginning intravenous catheters or venipuncture due to the excessive fatty deposits directly under the skin. Geriatric Patients as a general rule have thinner or less flowing veins and are often anemic causing blood flow restriction.

Specifically, for compromised patients with poor vessel quality, extreme care is needed to promote vasodilation to facilitate venipuncture without causing undue harm to already damaged vessels and tissues. It is important to provide a controlled warming of the tissues within the therapeutic range of temperature and duration of action to avoid tissue damage or ineffective treatment.

Infants and children tend to have tiny veins causing difficulty in gaining access to an injection or insertion site of the first stick. Trauma patients are often compromised physiologically, in shock, or experiencing the cause and effect sequela of resuscitation and/or hypoperfusion/reperfusion resulting in myriad detrimental side effects to the circulatory system such as damaged, leaky blood vessels that are near to impossible to puncture or catheterize. However, successful and fast venipuncture and catheterization are crucial to preserving life and organ function in these individuals. Hospitalized individuals, where doctors are checking blood levels on a regular, daily and a multiple times per day basis may have problematic issues with getting their blood drawn. For all these individuals, venipuncture can involve more than one needle stick. Again, this causes pain, discomfort and for many, an emotional trauma associated with the medical profession and specifically, having blood drawn or an intravenous therapy started. In addition, the costly affect to the hospital, clinic or center drawing the blood can become cumbersome with additional needles, alcohol swabs, bandages, and most costly the time for personnel with the patient.

It is known that warming the skin in an area to be punctured increases capillary action by dilating the blood vessels and consequently increases the rate of blood flow to the target area. The National Committee for Clinical Laboratory Standards specifically lists warming of the puncture site as part of the skin puncture procedure when dealing with neonatals and infants when pricking their heel for the typical newborn tests. Also, the Handbook of Phlebotomy Hospitals throughout the United States almost universally practice pre-warming of an intended puncture site when dealing with neonatal infants and pricking their heel for the typical newborn tests. Various forms of the warming device for an infant's heel have previously been patented. For example, see U.S. Pat. No. 5,143,048 to Cheney, U.S. Pat. No. 5,184,613 to Mintz, U.S. Pat. No. 6,723,115 to Daly, and others. While these present inventions have utility as a heel warmer for newborns, and some may be used in older children and even adults, they are only specified to the area of the heel of the foot in a heel stick medical procedure. Other forms of warming devices for promoting vasodilation that have previously been disclosed include: U.S. Publication No. 2012/0078223 to Spiegel disclosing a disposable warming garment for promoting vasodilation; U.S. Publication No. 2009/0299442 to Vergona et al. discloses a warming blanket with several pockets to hold disposable warming devices; and U.S. Publication No. 2008/0147152 to Quincy et al. disclosing a self-activated thermal warming device for use in sports, medical procedures, recreational use, or in the food industry.

Other possibly relevant patents include U.S. Pat. Nos. 4,229,833; 4,736,088; 5,909,801; 5,342,412; 6,052,824; 6,155,263; D674,106; 2011/0314581; 2012/0240918; 2012/0266351.

Existing devices are limited due to the failure to provide controlled generation of heat within therapeutic range of temperature and duration of action. In fact, the number one cause of recall and iatrogenic patient injury from warming devices is burns because of uncontrolled heating occurring with these devices (i.e. devices reaching temperatures outside the therapeutic range or being applied for extended periods). Existing devices are also limited due to the use of materials that don't facilitate non-traumatic compression, and/or inflexible materials that result in undesirable mobility, and/or baggy design that precludes a necessary fit.

BRIEF SUMMARY OF THE INVENTION

The present invention relates generally to a disposable self-warming apparatus such as but not limited to a sleeve with an attached tourniquet that preferentially allows for a method of warming human body parts to induce vasodilation, induce vessel engorgement and increase local blood pressure to foremost produce the ease of venipuncture. For cases where venipuncture or intravenous catheter insertion is desired, the invention preferably includes a patch of topical anesthetic to further minimize patient pain during such procedures.

In one embodiment, the invention is generally and preferably directed to a warming apparatus such as but not limited to a sleeve with an attached tourniquet that preferably Allows for a method of warming distal limbs and a method to induce vasodilation and a method of vessel engorgement and increased local blood volume/pressure to preferentially produce the ease of venipunctures for multiple strategic sites on the human body, such as but not limited to the brachial vein, the ulnar and the radial veins in the forearm that extend into the hand where blood is normally drawn from and intravenous therapy is inserted in preparation for a medical procedure. More specifically, the invention preferably relates to a disposable apparatus that preferably fastens to a hand and forearm for first warming skin, veins and arteries located in the hand and forearm, and then preferably using an attached tourniquet to reduce venous blood flow from the intended site to promote vessel engorgement, increase local blood pressure thereby creating resistance enabling a medical provider to easily identify potential vessels for venipuncture or intravenous catheter placement. A needle would preferably be inserted into a strategic site in order to draw blood, obtain a sample or start intravenous therapy that is an infusion of liquid substances directly into a vein intravenously. The invention may also include adhesive patches with topical anesthetic at the aforementioned strategic sites so that once vasodilation is achieved, the venipuncture process can be completed with minimal patient pain.

The apparatus preferably comprises of a generally square or rectangle shaped flexible pouch with a winged elongated side defining an internal chamber containing an absorbent warming composition, which preferably activates by contact with an aqueous liquid held safely inside an activation cell until manually manipulated to rupture and breach the activation cell, preferably mix with the warming composition, and preferably achieve the warming reaction of 104-105 degrees Fahrenheit for a period of 10 minutes, the standard desired adult therapeutic range of temperature and duration of action. The apparatus preferably has a hole so that the patient's thumb fits through, the apparatus also preferably wraps around a patient's forearm and can be preferably secured by means including by not limited to Velcro straps, creating a form fit for different sized adult patients, thereby preferably holding the apparatus in place at the thumbs, below the wrist and just below the bend at the elbow. However, it is reasonable that the device could be configured smaller to fit pediatric patients or even configured to fit the distal lower extremities to accommodate neonatal patients, as the technology is generally applicable. The device can also be sized to accommodate the limb of an animal for veterinary use.

When the area preferably covered by the apparatus is heated; a means of compressing venous blood flow, is preferably tightened so that vessel engorgement and increased local blood pressure occurs to facilitate ease of access of an injection or insertion site. This invention is preferably intended for single use, allowing for easy disposal without the need for disinfection. The apparatus is also preferably packaged in a single system that will preferably replace simple traditional, traumatic rubber tourniquets that are commonly used and include means for easily identifying injection or insertion sites for pain free and cost effective venipuncture.

In one embodiment, an apparatus with a heat transfer medium can provide an activation cell filled with an aqueous liquid that is preferably manipulated manually in order to break. Once broken, the aqueous liquid is preferably activated by mixing with a warming composition that preferably fills the apparatus. The apparatus preferably fits over the thumb of a patient's hand and preferably removably attaches in place such as by means including but not limited to buckles, fasteners, Velcro, preferably covering the entire area beneath the fingers to the base of the forearm (e.g., almost to the elbow).

This apparatus will preferably heat to a temperature of about 105 degrees Fahrenheit and preferably stay heated for a period of 10 minutes, preferably allowing the area covered by the apparatus to be heated and remain heated. When the area preferably covered by the apparatus is heated, a means of compression, such as but not limited to a tourniquet or a rubber band tied at the top of the apparatus may be used to preferably constrict and compress blood flow, is preferably tightened to that vessel engorgement, localized increase of blood pressure facilitates the location of an injection or insertion site. This invention is preferably intended for single use, allowing for easy disposal without the need for disinfection. The apparatus is preferably packaged in a single system that will preferably replace simple rubber tourniquets that are commonly used and include means for easily identifying injection or insertion sites for pain free and cost effective venipuncture.

The invention further states that this apparatus will preferably provide a simpler method of identifying veins and arteries so that medical professionals can do their job more efficiently by preferentially increasing first-stick success rate of inserting a needle or catheter into a patient's skin in order to obtain a sample of blood or begin intravenous therapy, thereby reducing cost and improving patient comfort. The invention preferably induces vasodilation by applying heat to an area and then further preferentially reducing the efflux of blood flow from the veins with the tourniquet to facilitate venipuncture by inducing vasodilation, vessel engorgement and increased local blood pressure were venipuncture or intravenous catheter insertion is desired. The apparatus and method will preferably provide comfort to the patient with heat to the area prior to the introduction of the needle or catheter, a topical anesthetic applied to the area prior to introduction of the needle or catheter as well as the resulting knowledge of the Phlebotomist's "job made easier with the new technology of applied therapeutic levels of heat and compression to increase first-stick success rate even on the worst veins!"

BRIEF DESCRIPTION OF THE SEVERAL VIEWS OF THE DRAWINGS

For a further understanding of the nature, objects, and advantages of the present invention, reference should be had to the following detailed description, read in conjunction with the following drawings, wherein like reference numerals denote like elements and wherein.

DETAILED DESCRIPTION OF THE INVENTION

Figure 1:
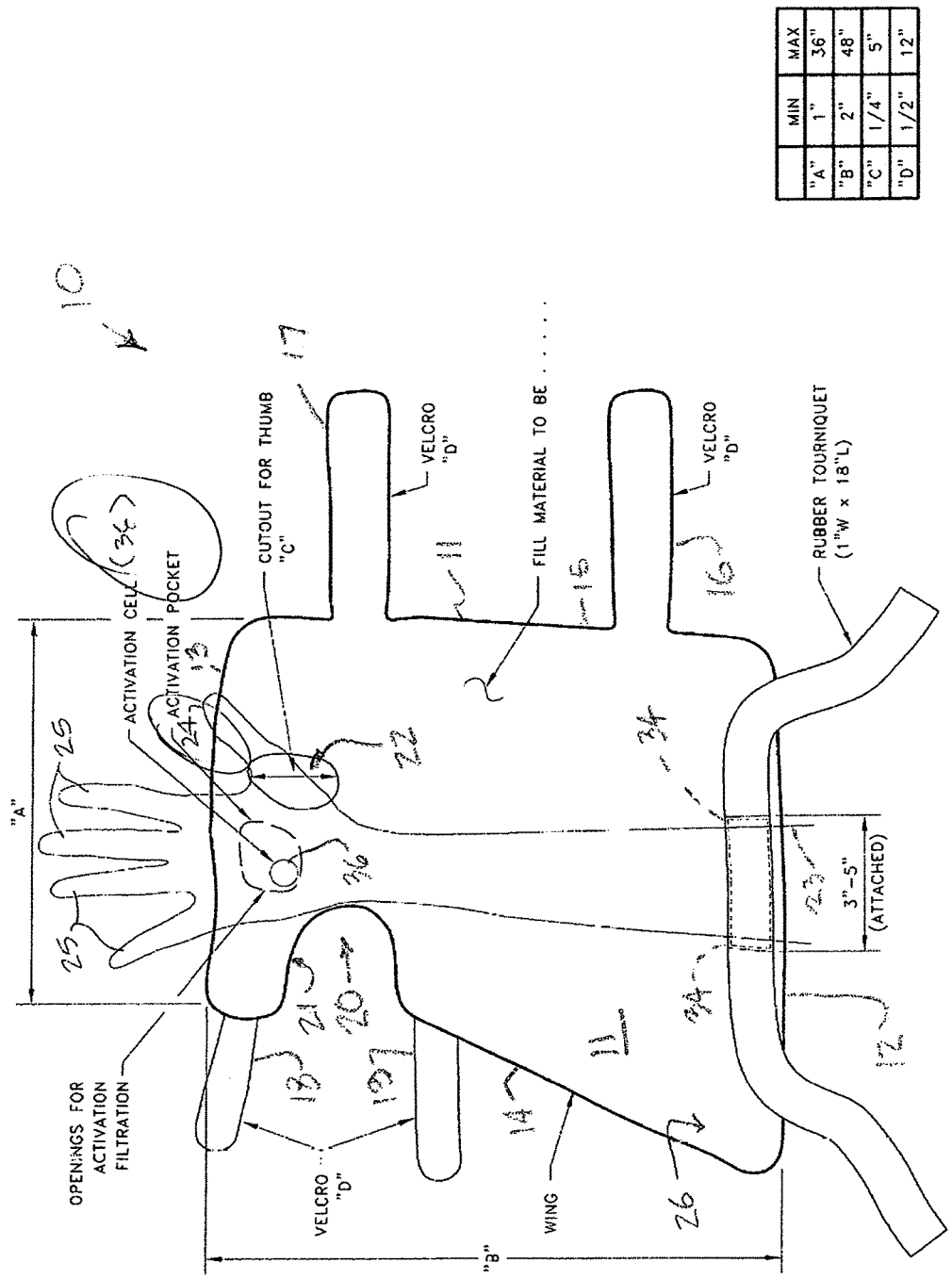
FIG. 1 is a top view of a preferred embodiment of the apparatus opened up around a patient's arm and hand.

FIGS. 1-4 show the preferred embodiment of the form-fitting apparatus of the present invention designated generally by numeral 10. Apparatus 10 is used to warm a patient's skin and deeper tissues prior to an intravenous insertion of a needle from a patient's skin surface into the patient's vein. The apparatus includes a panel 11 having a proximal edge 12 and a distal edge 13. Side edges include first side edge 14 and second side edge 15. The edges 12, 13 can be generally parallel. The edges 14, 15 can be angled relative to one another to form an acute angle (see FIG. 1).

Figure 6:
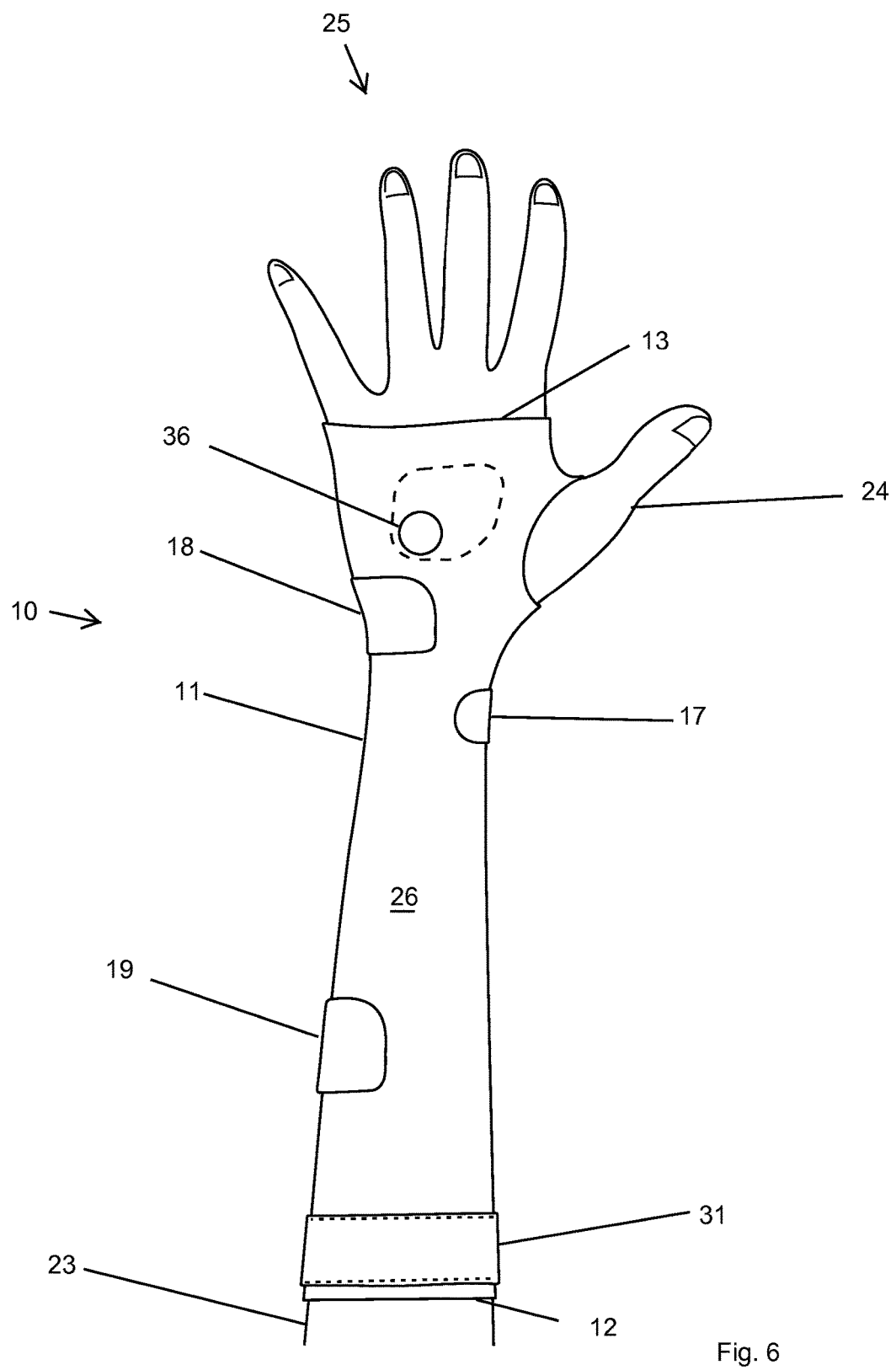
FIG. 6 is a top view of a preferred embodiment of the apparatus of the present invention installed on a patient's arm.
Figure 7:
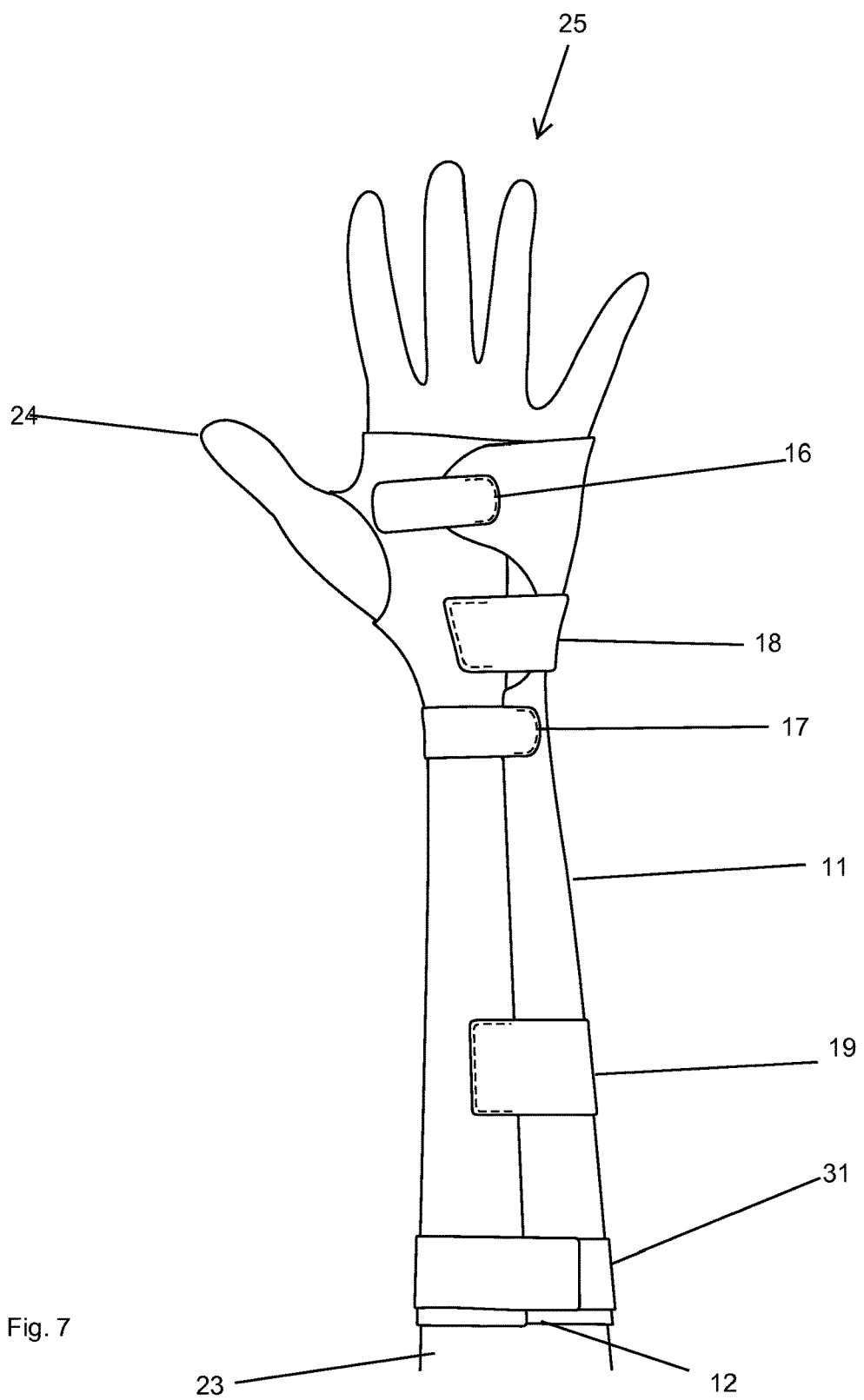
FIG. 7 is a bottom view of a preferred embodiment of the apparatus of the present invention installed on a patient's arm; and, FIG. 8 is a perspective view of an alternate embodiment of the apparatus of the present invention.

A plurality of straps are attached to the panel 11. These include straps 16, 17 attached to panel 11 at side edge 15 and straps 18, 19 attached to edge 14 as shown in FIG. 1. As shown in FIG. 1, dimension A is the width of the hand portion and dimension B is the overall length. The strap 16, 17 can be spaced farther apart than the spacing of straps 18 and 19. A recess 20 can be provided on edge 14 in between straps 18, 19. The recess 20 is formed by curved edge 21 in edge 14. The recess or cut out 20 is provided for the patient's thumb 24. Upon wrapping of panel 11 about a patient's forearm 23 (as shown in FIGS. 6 and 7), the strap 17 traverses the edge 21. The angled side 14 allows the apparatus to be adjusted to fit the forearm of a large range of patient sizes.

A cut out or opening 22 can be formed through panel 11 for insertion of a patient's thumb 24 there through. Thus, the thumb 24 is exposed, passing through opening 22 and occupying cut out or recess 20. The panel 11 is designed to wrap around a patient's forearm 23, extending between a patient's elbow and the patient's fingers 25, thus substantially covering the patient's forearm 23 as shown in FIGS. 1, 6 and 7.

Figure 4:
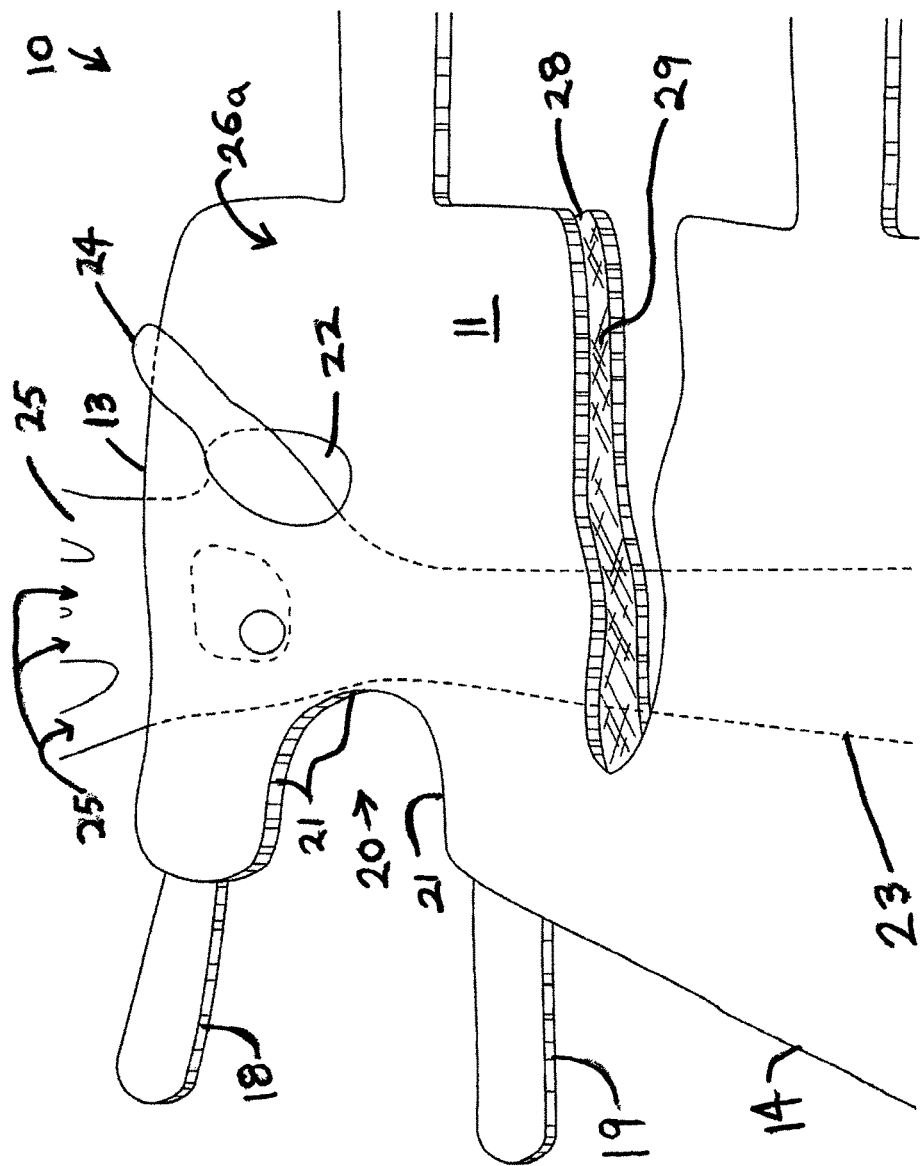
FIG. 4 is a partial cutaway view of the preferred embodiment of the apparatus of the present invention.

Panel 11 provides an upper surface 26 and a lower surface 27. A cavity 28 can be provided in between upper and lower surfaces 26, 27, as shown in FIG. 4. Cavity 28 is filled with a heat transfer medium such as an exothermic material 29 that can be activated in order to generate heat. Such exothermic material is commercially available. It is commonly used for hand warmer pads and foot warmer pads as examples. Some such warmer products are sold under the trademark "Grabber". In one embodiment, an activation cell 36 is contained within a portion of cavity 28. Rupture type cell configurations, as are commonly known, are configured to be broken to activate the heat transfer medium or exothermic material 29 that occupies a majority of the cavity 28 in between the upper and lower services 27, 29.

Figure 2:
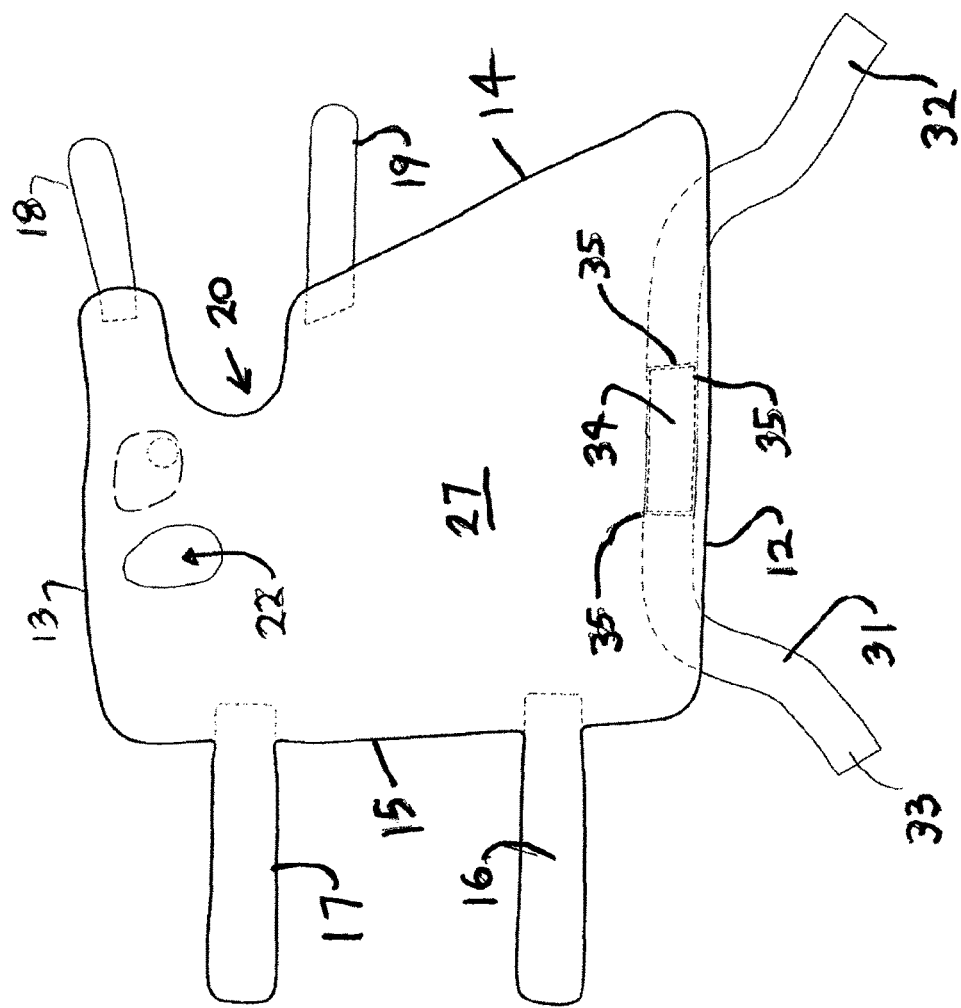
FIG. 2 is a top view of a preferred embodiment of the apparatus of the present invention.
Figure 3:
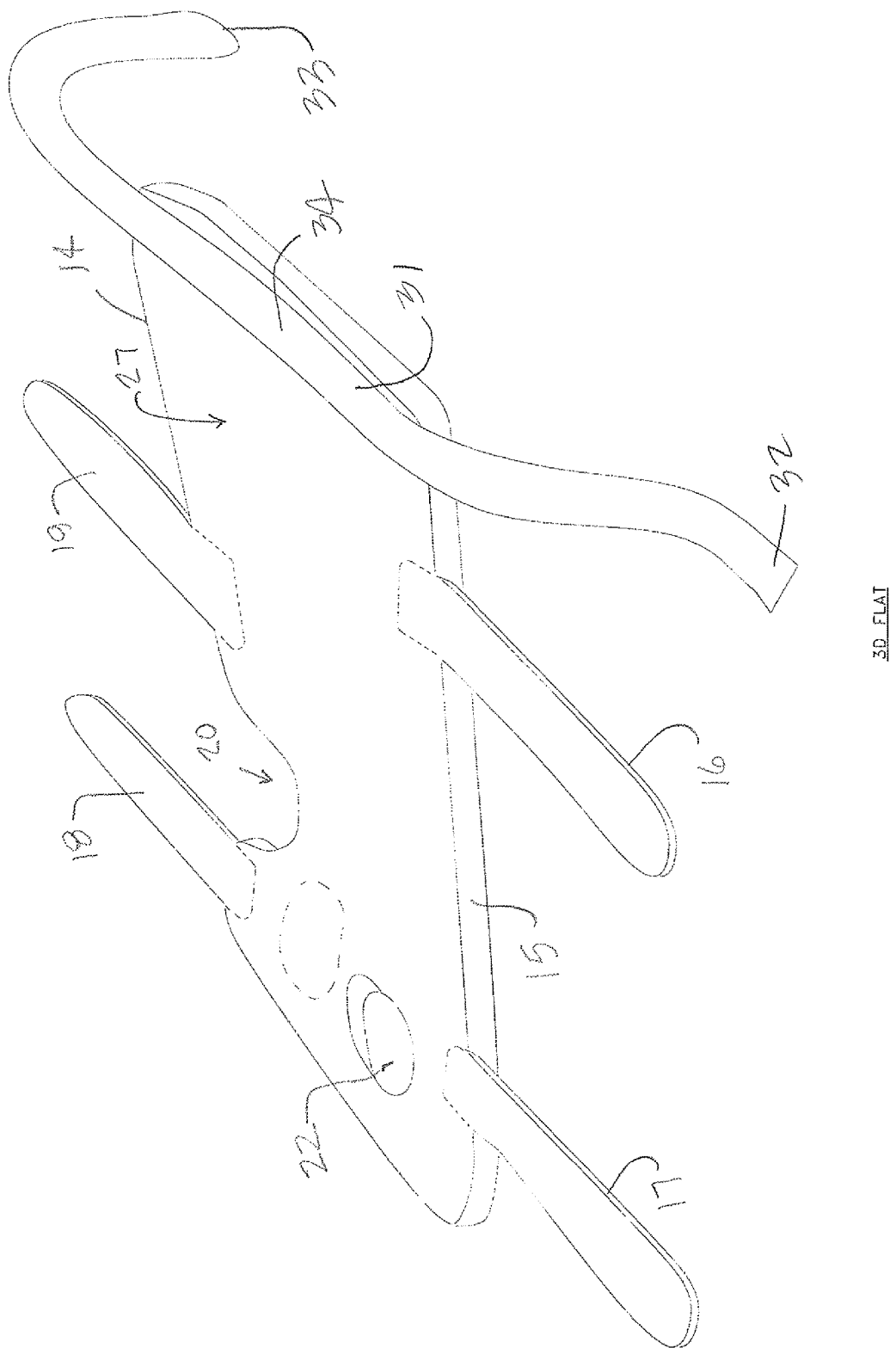
FIG. 3 is a perspective view of a preferred embodiment of the apparatus of the present invention.

A tourniquet or strap 31 is attached panel 11 next to proximal edge 12 as shown in FIG. 1. The strap 31 provides a first end 32 and a second end 33. The tourniquet or strap 31 is attached to the panel 11 using an attachment 34 which is shown as a rectangular area in FIG. 1. The attachment 34 can be adhesive or in the form of stitching 35 as shown in FIG. 2.

Figure 8:
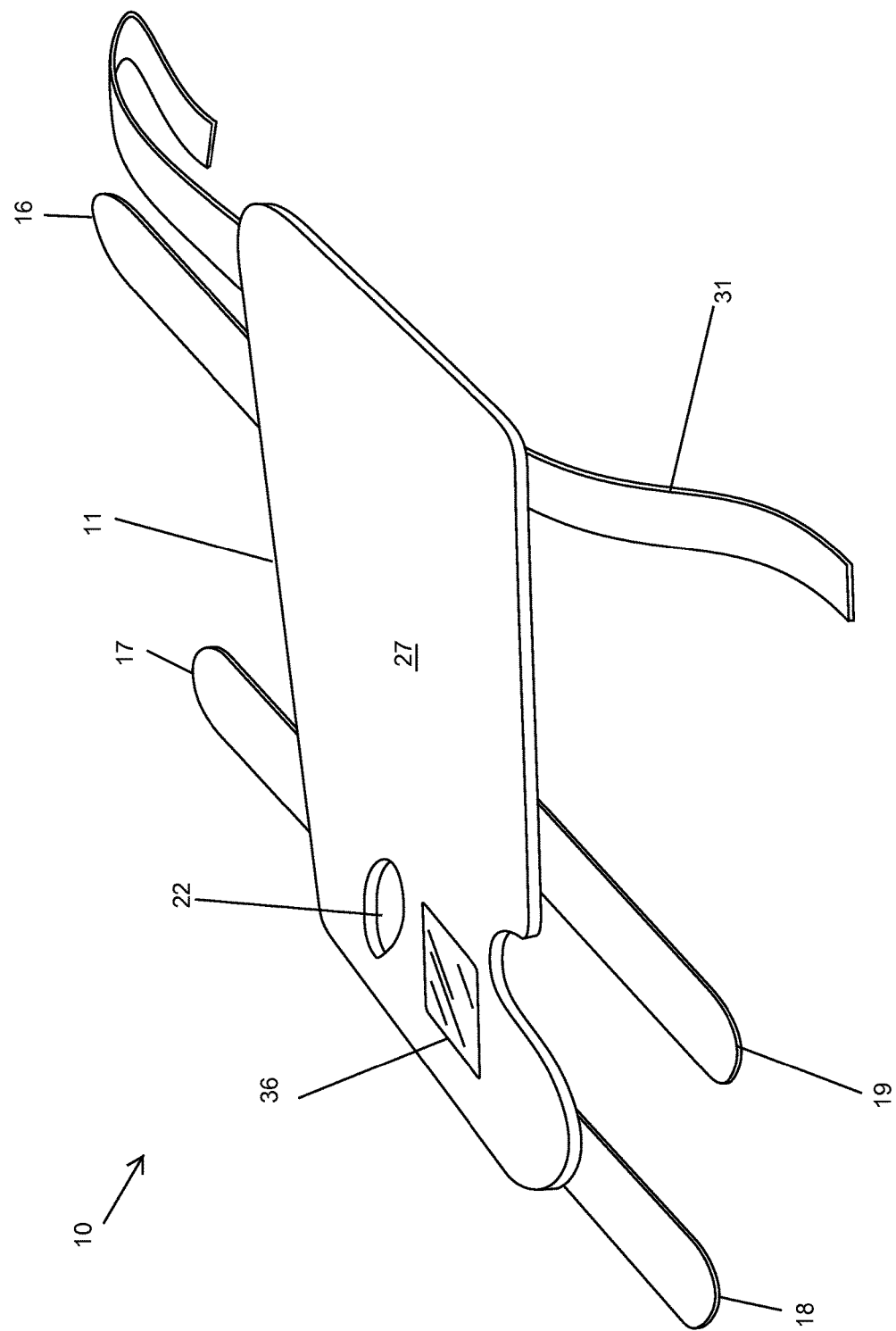

The invention may also include one or more adhesive patches 36 with topical anesthetic at various strategic sites (see FIG. 8), such as but not limited to the brachial vein, the ulnar and the radial veins in the forearm that extend into the hand where blood is normally drawn from and intravenous therapy is inserted in preparation for a medical procedure, so that once vasodilation is achieved, the venipuncture process can be completed with minimal patient pain.

Figure 5:
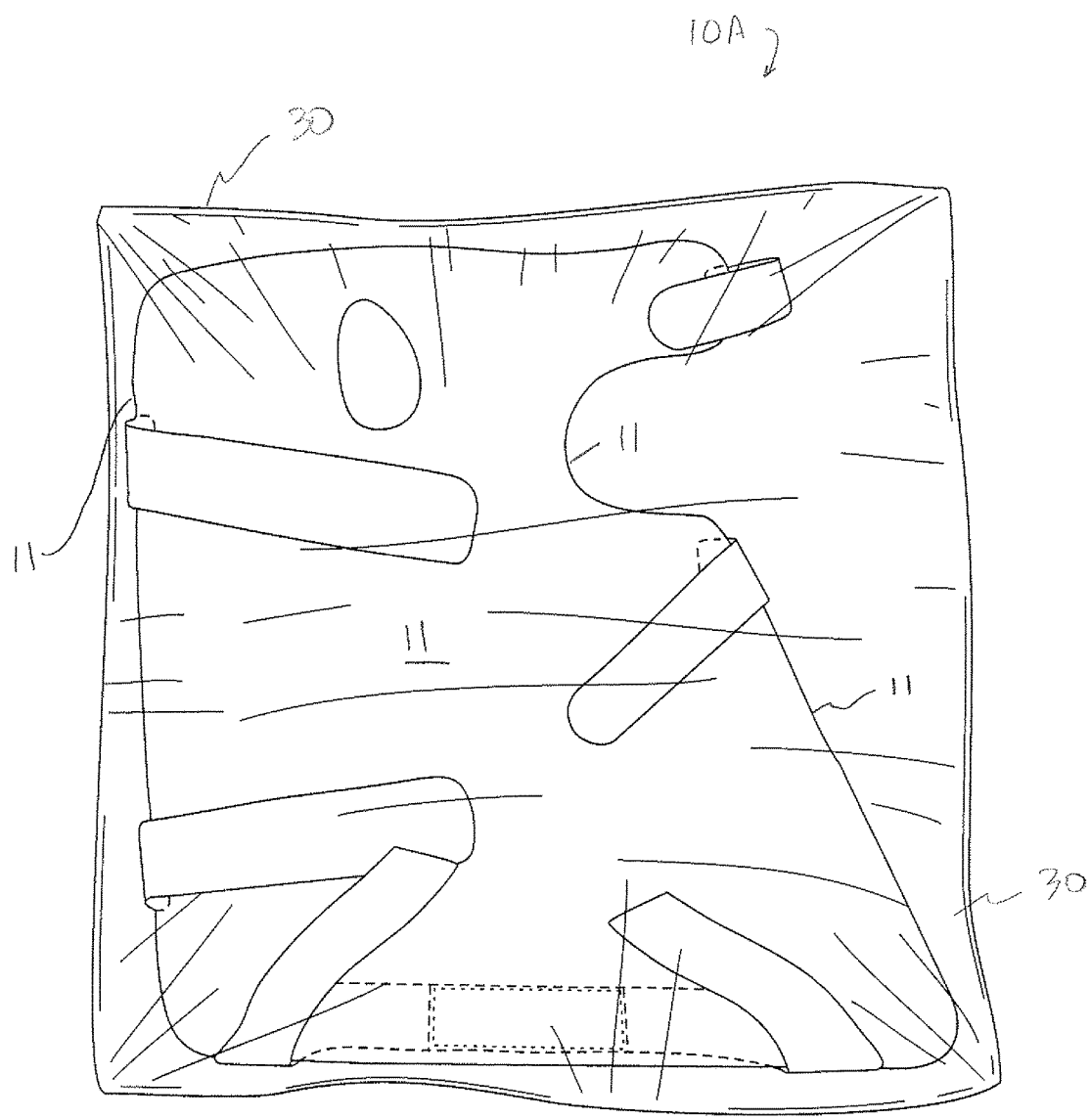
FIG. 5 is a top view of an alternate embodiment of the apparatus of the present invention in a folded position and encapsulated in an air tight or vacuum packed enclosure.

In a second embodiment shown in FIG. 5, the heat transfer medium or exothermic material 29 is an air activated material. In FIG. 5, the tourniquet apparatus is designated by the numeral 10A. An encapsulating cover foil pack, or vacuum pack cover or air free package 30 envelops the apparatus so that no air is able to interact with the heat transfer medium or exothermic material 29. A user removes the encapsulating cover foil pack, or vacuum pack or air free packaging 30 which enables air to make a contact with the heat transfer medium 29 and activate it. Such air activated heat transfer medium material is commercially available. In such a case of a heat transfer material 29 that is air activated, the cover or panel 11 would have some porosity so that the air was able to interface with the medium 29. Preferably, topical anesthetic, such as lidocaine, is included in the adhesive patch 36 to allow the apparatus 10 to numb all possible venipuncture sites on the patient. The exothermic material 29 is preferably a soft, flexible plastic, such as that manufactured by DeRoyal Industries, Inc.

The following is a list of parts and materials suitable for use in the present invention:

PARTS LIST:

| PART NUMBER | DESCRIPTION |
| --- | --- |
| 10 | tourniquet apparatus |
| 10A | tourniquet apparatus |
| 11 | panel |
| 12 | proximal edge |
| 13 | distal edge |
| 14 | first side edge |
| 15 | second side edge |
| 16 | strap |
| 17 | strap |
| 18 | strap |
| 19 | strap |
| 20 | recess |
| 21 | curved edge |
| 22 | cut out/opening |
| 23 | patient forearm |
| 24 | patient thumb |
| 25 | patient fingers |
| 26 | upper surface |
| 27 | lower surface |
| 28 | cavity |
| 29 | heat transfer medium/exothermic material |
| 30 | encapsulating cover/vacuum pack/air free package |
| 31 | tourniquet strap |
| 32 | first end |
| 33 | second end |
| 34 | attachment |
| 35 | stitching |
| 36 | adhesive patch |

All measurements disclosed herein are at standard temperature and pressure, at sea level on Earth, unless indicated otherwise. All materials used or intended to be used in a human being are biocompatible, unless indicated otherwise.

The foregoing embodiments are presented by way of example only; the scope of the present invention is to be limited only by the following claims.

The invention claimed is:

1. An apparatus for enabling intravenous insertion of a needle through a patient's skin surface into the patient's vein, comprising:
   a. a panel having proximal and distal end portions and first and second side portions, the panel having an internal cavity;
   b. a heat transfer material held in the internal cavity, the heat transfer material configured to generate a controlled, pre-determined level of heat with a temperature that is within therapeutic ranges of temperature and last for a therapeutic length of time for the purpose of promoting vasodilation;
   c. the panel including an elastic band placed next to the proximal end portion, wherein the elastic band is sized and shaped to encircle and apply compression to a limb of the patient, thereby reducing the efflux of venous blood flow at a position proximal to an intended intravenous injection site so that vessel engorgement and increased local blood pressure occurs;
   d. one or more straps that enable the panel to be secured to itself creating a flexible, form-fit to the patient's limb, said one or more straps are configured to provide a disassembled configuration such that when the panel is not secured to itself, the intended insertion or injection site is exposed while the elastic band of the panel remains positioned and fastened proximally and continues to reduce efflux of venous blood flow from the patient's limb.

2. The apparatus of claim 1 wherein the panel is generally trapezoidal in a first state, and curved in a second state when attached to the limb of a patient.

3. The apparatus of claim 2, wherein in the second state, the panel is configured to cover a majority of the patient's forearm.

4. The apparatus of claim 1 wherein the heat transfer material is a gel.

5. The apparatus of claim 1 wherein the heat transfer material is an exothermic material.

6. The apparatus of claim 5 wherein the heat transfer material is activated by exposure to air.

7. The apparatus of claim 1 wherein the heat transfer material is a liquid.

8. The apparatus of claim 1 wherein the heat transfer material is a chemical that is activated to generate heat after activation.

9. The apparatus of claim 1 wherein the distal end portion of the panel has an opening sized and positioned to receive the patient's thumb.

10. The apparatus of claim 1, further including one or more adhesive patches, the adhesive patches containing a therapeutic amount of topical anesthetic.

11. The apparatus of claim 1 wherein the panel is sized to extend from a patient's elbow to a patient's wrist.

12. The apparatus of claim 1 wherein the panel is sized for veterinary use.

13. An apparatus for enabling intravenous insertion of a needle through a patient's skin into the patient's vein, comprising:
   a. a wrap having proximal and distal end portions and first and second side portions, the wrap having and interior cavity;
   b. a heat transfer material contained in the cavity, the heat transfer material constituted to generate a controlled, pre-determined level of heat with a temperature that is within therapeutic ranges of temperature and last for a therapeutic length of time for the purpose of promoting vasodilation;
   c. an elastic band attached to the wrap next to the proximal end, wherein the elastic band is sized and shaped to encircle and apply compression to a limb of the patient thereby reducing the efflux of blood flow at a position proximal to an intravenous injection site so that vessel engorgement and increased local blood pressure occurs;
   d. connectors that enable the wrap to be secured to itself creating a form-fit to the patient's limb; wherein said connectors are configured to provide a disassembled configuration such that when disassembled the injection site is exposed while the elastic band remains positioned and fastened proximally to reduce the efflux of blood flow from the patient's limb.

14. The apparatus of claim 13 wherein the wrap is movable to a flat, generally trapezoidal position.

15. The apparatus of claim 13 wherein the heat transfer material is one of a liquid, a gel, an exothermic material activated by contact with another, second material, or a chemical that is activated to generate heat after activation.

16. The apparatus of claim 13 wherein the wrap has one or more openings sized and shaped to receive a digit of the patient's hand.

17. The apparatus of claim 13, further including one or more patches containing a therapeutic amount of topical anesthetic.

18. The apparatus of claim 13 wherein the wrap is configured to cover the majority of the patient's lower leg.

19. The apparatus of claim 18, further including one or more adhesive patches covered with a removable film, the adhesive patches containing a therapeutic amount of topical anesthetic.

20. The apparatus of claim 13 wherein the wrap is sized to extend from the patient's elbow to the patient's wrist.

21. The apparatus of claim 13 wherein the wrap is sized for veterinary use.

22. A method for inducing vasodilation for venipuncture comprising the steps of:
   a. providing a wrap having an internal pouch, an exothermic material contained within the pouch, the exothermic material is activatable from a first ambient temperature to a second therapeutic temperature, an elastic band carried by the wrap, and connectors;
   b. activating the exothermic material so that it generates a controlled level of heat at the second therapeutic temperature for ten minutes;
   c. placing the wrap over a patient's thumb and securing the wrap around the patient's arm;
   d. tying the elastic band to the patient's arm to induce vessel engorgement and increase local blood pressure;
   e. disassembling the connectors such that the intravenous injection site on the patient's arm is exposed while the elastic band and a part of the wrap remains fastened and positioned such that the elastic band continues to compress the venous blood flow from the patient's arm;
   f. identifying and accessing a vein for venipuncture.

23. The method of claim 22 wherein the heat transfer material is activated by exposure to air.

24. The method of claim 22 further comprising the step of applying anesthetic to the venipuncture site.

* * * * *

UNITED STATES PATENT AND TRADEMARK OFFICE
CERTIFICATE OF CORRECTION

| | | |
|---|---|---|
| PATENT NO. | : 10,272,211 B1 | Page 1 of 1 |
| APPLICATION NO. | : 14/153845 | |
| DATED | : April 30, 2019 | |
| INVENTOR(S) | : Cooke et al. | |

It is certified that error appears in the above-identified patent and that said Letters Patent is hereby corrected as shown below:

On the Title Page

Item (12) replace "Cooke et al." with --Rearick et al.--.

Item (71) Applicants and (72) Inventors section should read:
--Cathleen Rearick, Metairie, LA (US); Dian Rubin Cooke, Franklin, TN (US)--.

Signed and Sealed this
Sixteenth Day of July, 2019

Andrei Iancu
*Director of the United States Patent and Trademark Office*